(12) United States Patent
Horn et al.

(10) Patent No.: US 7,943,300 B2
(45) Date of Patent: May 17, 2011

(54) METHOD FOR IMPROVED PROTEIN EXPRESSION IN BACTERIA BY MONITORING AND MODULATING PROTEIN FOLDING

(75) Inventors: Uwe Horn, Rottleben (DE); Ulrike Riesenberg, Jena (DE); Wolfgang Strittmatter, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 916 days.

(21) Appl. No.: 10/482,728

(22) PCT Filed: Jul. 3, 2002

(86) PCT No.: PCT/EP02/07346
§ 371 (c)(1),
(2), (4) Date: Jan. 5, 2004

(87) PCT Pub. No.: WO03/004698
PCT Pub. Date: Jan. 16, 2003

(65) Prior Publication Data
US 2004/0185528 A1    Sep. 23, 2004

(30) Foreign Application Priority Data
Jul. 6, 2001    (EP) ..................................... 01116371

(51) Int. Cl.
*C12Q 1/68*    (2006.01)
*C12Q 1/66*    (2006.01)
*C12N 1/20*    (2006.01)

(52) U.S. Cl. .............................. 435/6; 435/252.3; 435/8

(58) Field of Classification Search .......................... None
See application file for complete search history.

(56) References Cited

U.S. PATENT DOCUMENTS

| | | | |
|---|---|---|---|
| 6,410,270 B1 * | 6/2002 | Strittmatter et al. | 435/69.6 |
| 6,630,317 B1 * | 10/2003 | Pluckthun et al. | 435/7.4 |
| 2004/0170976 A1 * | 9/2004 | Lesley et al. | 435/6 |

OTHER PUBLICATIONS

Danese et al. Accumulation of the Enterobacterial Common Antigen Lipid II Biosynthetic Intermediate Stimulates degP Transcription in Eschericahi coli. J. Bac. 180(22): 5875-5884, 1998.*
Waldo, G. Genetic screens and directed evolution for protein solubility. Current Opinion in Chem. Biol. 7:33-38, 2003.*
Everest et al. Expression of LacZ from the htrA, nirB and groE promoters in a *Salmonella* vaccine strain: influence of growth in mammalian cells. FEMS Micro. Letters 126: 97-102, 1995.*
Strauch et al. Characterization of degP, a gene required for proteolysis in the cell envelope and essential for growth of *Escherichia coli* at high temperature. J. Bac. 171(5): 2689-2696, 1989.*
Billard et al. Bioluminescence-based assays for detection and characterization of bacteria and chemicals in clincial laboratories. Clinical Biochem. 31(1): 1-14, 1998.*
Krebber et al. Inclusion of an upstream transcriptional terminator in phage display vectors abolishes background expression of toxic fusions with coat protein g3p. Gene 178: 71-74, 1996.*
Lipinska et al. The HtrA (DegP) protein, essential for *Escherichia coli* survival at high temperatures, is an endopeptidase. J Bacteriol. Apr. 1990;172(4):1791-7.*
Miles et al. In vivo enhancement of tumor radioresponse by C225 antiepidermal growth factor receptor antibody. Clin Cancer Res. Feb. 2000;6(2):701-8.*
Hayhurst et al. *Escherichia coli* skp chaperone coexpression improves solubility and phage display of single-chain antibody fragments. Protein Expr Purif. Apr. 1999;15(3):336-43.*
Caldas et al. Thermoprotection by glycine betaine and choline. Microbiology. Sep. 1999; 145 ( Pt 9):2543-8.*
Andreas Smeds et al: "Molecular characterization of a stress-inducible gene from lactobacillus helveticus" Journal of Bacteriology, Washington, DC, US, vol. 180, No. 23, Dec. 1998 pp. 6148-6153, XP002113159.
Danese Paul N et al: "Accumulation of the enterobacterial common antigen lipid II biosynthetic intermediate stimulates degP transcription in *Escherichia coli*." Journal of Bacteriology, vol. 180, No. 22, Nov. 1998, pp. 5875-5884, XP002245229.
Missiakas D et al: "Protein misfolding in the cell envelope of *Escherichia coli*: new signaling pathways" TIBS Trends in Biochemical Sciences, Elsevier Publication, Cambridge, EN, vol. 22, No. 2, Feb. 1, 1997, pp. 59-63, xP004050132.

* cited by examiner

*Primary Examiner* — Michele K Joike
(74) *Attorney, Agent, or Firm* — Millen, White, Zelano, Branigan, P.C.

(57) ABSTRACT

This invention relates to a new method for improving functional protein expression whereby the folding process is monitored by online measurement and, if required, the protein folding is influenced by adding folding promoting agents and/or co-expression of the periplasmic chaperone (Skp). In this respect, the invention offers a technology to improve the yield of functionally expressed recombinant proteins.

15 Claims, 9 Drawing Sheets

Figure 1 stop        *degP* - Promotor →
*dgt*
TAA CCAGGC<u>TTTTGTAAAGACGAAC</u>AATAA<u>ATTTTTACCTTTTGCAGAAA</u>CTTTAGT -35                      -10
TCG<u>GAACTT</u>CAGGCTATAAAACGAA<u>TCTGAA</u>GAACACAGCAATTTTGCGTTATCTGTT SD       start *degP* →
AATC<u>GAGA</u>CTGAAATAC <u>ATG</u>...           SEQ. ID. 1
             ↓
          * start *luc*<sup>+</sup> →
          <u>CC ATG G</u>AA GAC GCC        SEQ. ID. 2
               *Nco*I   E   D   A

*Nsi*I
degP_fw:     5' TGC<u>ATGCAT</u>CCAGGCTTTTGTAAAGACGAAC 3'     SEQ. ID. 3

*Nco*I
degP_back:    5' TCATG<u>CCATGG</u>ATTTCAGTCTCGATTAACAGATAACG 3'    SEQ. ID. 4

Figure 4

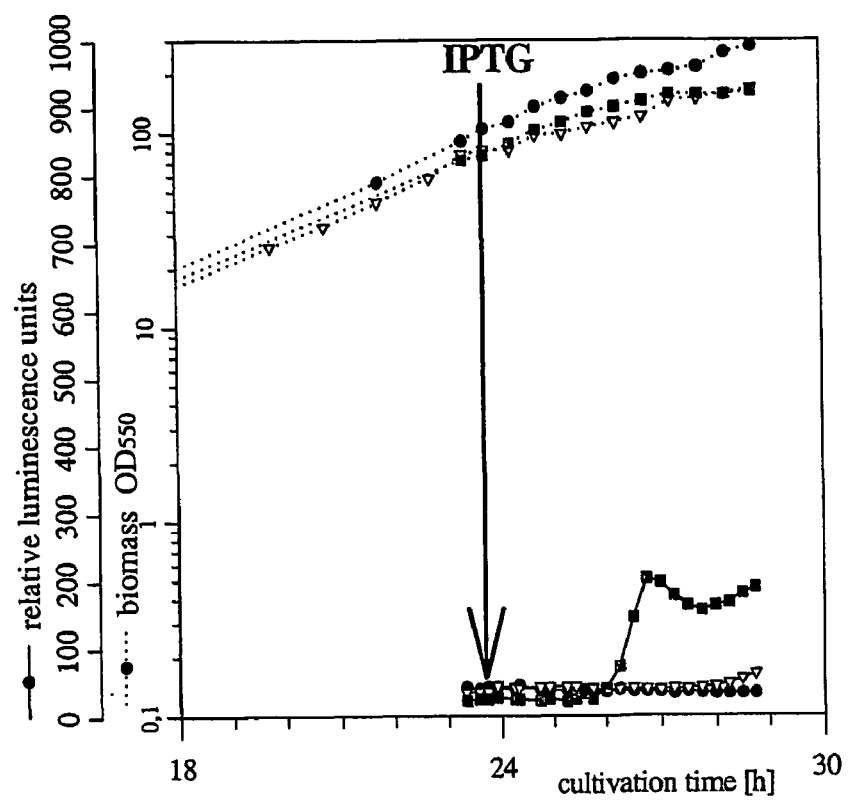

····•···· biomass (start of feeding simultaneously to the cultivation)
····▽···· biomass (start of feeding simultaneously to miniantibody induction)
····■···· biomass (start of feeding 2h after miniantibody induction)
——•—— luminescence (start of feeding simultaneously to the cultivation)
——▽—— luminescence (start of feeding simultaneously to miniantibody induction)
——■—— luminescence (start of feeding 2h after miniantibody induction)

Figure 8

```
P_lac_native
SEQ. ID. 5   5' CCCACCTCAA CgCAATTAAT gTgAgTTAgC TCACTCATTA ggCACCCCAg gCTTTACACT TTATgCTTCC ggCTCgTATg P_lac_C                              * (L8)
SEQ. ID. 6   5' CCCACCTCAA CgCAATTAAT gTAAgTTAgC TCACTCATTA ggCACCCCAg gCTTTACACT TTATgCTTCC ggCTCgTATg P_lac_CU                                                                                              *
SEQ. ID. 7   5' CCCACCTCAA CgCAATTAAT gTgAgTTAgC TCACTCATTA ggCACCCCAg gCTTTACACT TTATgCTTCC ggCTCgTATA P_lac_CTU                                              Δ  *  *Δ      Δ                                *
SEQ. ID. 8   5' CCCACCTCAA CgCAATTAAT gTgAgTTAgC TCACTCATTA ggCACCCCAg g-TTGACAA- -TATgCTTCC ggCTCgTATA
```

US 7,943,300 B2

METHOD FOR IMPROVED PROTEIN EXPRESSION IN BACTERIA BY MONITORING AND MODULATING PROTEIN FOLDING

FIELD OF THE INVENTION

This invention relates to a new method for improving functional protein expression whereby the folding process is monitored by online measurement and, if required, the protein folding is influenced by adding folding promoting agents and/or co-expression of the periplasmic chaperone Skp. In this respect, the invention offers a technology to improve the yield of functionally expressed recombinant proteins.

BACKGROUND OF THE INVENTION

Over expression of recombinant gene products in the periplasm of Escherichia coli results is frequently associated with unfolded or misfolded protein and may involve degradation by cellular proteases. Furthermore, uncontrolled leakage or lysis of cells, caused by misfolding can inhibit fermentation processes directly or by an overflow of foam. Therefore, several strategies have been developed to improve the expression and folding properties of proteins in the periplasm of Escherichia coli. At first, a successful expression and folding of recombinant proteins is closely linked to the choice of optimal regulatory sequences, e.g. promoter strength, ribosome binding sites and signal peptides[1-3]. Application of folding strategies mainly refer to feeding of folding promoting agents[4-10], to the coexpression of molecular chaperones and to adding folding catalysts[11-15].

Folding promoting agents such as glycine, betaine and hydroxyectoine are known protein protectants in the art[48-50]. In general it is believed, that these compounds do not strengthen the protein conformation by specific binding as would a substrate or an inhibitor. The stabilizing effect of these compounds has been attributed mainly to their exclusion from the protein surface, hence leading to 'preferential hydration' of the protein, or 'preferential exclusion' of the additive from the protein surface. However the stabilizing phenomenon is a rather complex one, and it has to be pointed out, that there is no single mechanism responsible for the stabilization but a multitude of stabilizing and destabilizing interactions besides the preferential exclusion mechanism.

In addition to using extrinsic folding promoting agents the protein itself can be improved either by molecular modeling or directed evolution, here and elsewhere experiments performed have used scFv antibody fragments[16-19].

It has to be pointed out that none of all the individual strategies is generally successful and therefore the folding of proteins has to be improved sequentially and case by case. This requires technologies for direct folding monitoring, which ideally are independent of functional assays. The current invention delivers the technical solution to this problem. In contrast to recent works[20-21] the invention does use the native stress response to misfolded protein in the periplasm of Escherichia coli, regulated by two partially overlapping pathways, the sigma E response and the Cpx signal transduction system[24]. Sigma E is tightly regulated by three genes, rseA, rseB and rseC[25]. The transmembrane protein RseA senses and transmits information to sigma E, negatively regulated by the interaction with the periplasmic RseB and positively by RseC, respectively, located in the inner membrane. The Cpx two-component signal transduction system consists of a membrane sensor histidine kinase CpxA and a cytoplasmic response regulator CpxR. Misfolded protein leads to autophosphorylation of CpxA followed by a phosphotransfer to CpxR, allowing CpxR to function as a transcriptional activator[27-29]. Both the sigma E and the Cpx response induce several genes involved in protein folding and degradation in the case of periplasmic misfolding. The Cpx signal transduction system coordinates the activation of DsbA, PpiA and PpiD[20-30], whereas sigma E regulates the transcription of at least 10 gene products, including even sigma E, sigma 32 and fkpA[31-35]. Only degP (htrA) is regulated by both systems, indicating that degP is a central element in the periplasmic misfolding management.[36-40]. In this respect, the invention among other aspects demonstrates that a degP promoter based reporter system is very suitable for kinetic studies of protein misfolding in the periplasm of Escherichia coli and allows an effective use in combination with different protein folding strategies.

SUMMARY OF THE INVENTION

The accumulation of unfolded or misfolded protein in the periplasm of Escherichia coli leads to the induction of the well known, tightly regulated periplasmic protease degP. Based on the A degP-promoter and a luciferase reporter gene an on-line measurement technology has been developed, allowing in vivo kinetic studies of protein misfolding during fermentation processes. The technology was validated by periplasmic expression of a recombinant miniantibody specific for the human EGF-receptor. Performing different feeding strategies with folding promoting agents and coexpression of the periplasmic chaperone Skp we demonstrated the amount of functional protein to be indirectly proportional to the on-line luciferase signal representing the misfolded one. In this respect, the technology offers a simple tool to evaluate and improve the yield of functionally expressed proteins in the periplasm, depending on the used folding strategy.

DETAILED DESCRIPTION OF THE INVENTION

As many eucaryotic proteins retain their full biological activity in a post translationally nonmodified form as well their functional expression in Escherichia coli is an established strategy. Unfortunately, the correct folding of recombinant proteins in the periplasm of Escherichia coli is poorly understood and often interferes with the expression of functional protein. To tackle this problem, this invention presents a new technology allowing in vivo kinetic studies of protein misfolding. The technology helps to understand and monitor when and under which conditions misfolding does occur thus allowing to implement strategies for improving folding of the target protein.

The inventions technology is based on the promoter of the well known periplasmic protease DegP, which plays a key role in the periplasmic protein misfolding management. In this respect prior works implies, that the response to misfolded periplasmic protein after a heat shock at and above 42.degree. C. to be comparable with the stress caused by overexpressed misfolded recombinant proteins[23,31,45,46].

The on-line monitoring during the fermentation processes was realized by using luciferase luc$^+$ as a very sensitive reporter gene as part of a detection modul allowing an analysis in a total time of 90 s. This high resolution of measurements requires a short half-life of the reporter gene product. Due to the long half-life of green fluorescence protein (GFP) this protein is not applicable, however it turn out that unexpectedly Luc$^+$ is especially useful. We determined a half-life of about 5 minutes at our fermentation temperature of 26.degree. C. Thus a close correlation between the luciferase activity and the amount of the enzyme corresponding to the misfolded protein is guaranteed. Interestingly and not expected, our result indicate, that luciferase can diffuse through the *Escherichia coli* cell wall. Thus a rapid determination of the activity without any cell disruption can be performed. The use of pOU61 as coding vector of the degP-luciferase reporter cassette (resulting in plt1) generates additional advantages[43,44]. At a temperature below 30.degree. C. a genetically modified R1 origin tightly regulates the copy number at one copy per cell, leading to a gene dose comparable to the *Escherichia coli* chromosome. The encoded par locus prevents plasmid loss during cell division. The R1 origin is compatible with the colE1 derivate used in a cotransformed second plasmid for the expression of recombinant miniantibodies. Furthermore the use of pill in a dual plasmid system allows similar investigations of additional proteins without any additional cloning steps.

Recent works described a method for an in vivo folding monitoring and a protein-folding assay for cytoplasmic proteins.[20,21]. These methods are based on a fusion of a reporter protein to the target protein. Either the GFP or the .alpha.-fragment of the .beta.-galactosidase (to achieve an .alpha.-complementation with the larger .omega.-fragment) may be used as reporter proteins. Both methods are practicable for different proteins, but the construction of fusion proteins require, that the corresponding termini of the target protein is accessible. Moreover the folding properties of the target protein must not be impaired by the protein fusion.

In this respect the technology provides in this invention has major advantages over prior art. Namely, the usage of the native stress response to misfolded proteins allows studies of the folding of a target protein during recombinant expression without any additionally influencing factors. Additionally the effect of protein misfolding may be studied a kinetic manner. Thus not only the folding properties of the target protein can be improved, but also the regulatory sequences can be genetically optimized and the process parameters during the fermentation can be adapted. The term "functionally correct folding" means according to the invention that a protein expressed by a recombinant process has a folding (tertiary structure) that enables the protein to be fully or essentially active with respect to its proposed function.

Monitoring of the misfolding kinetics was evaluated by expressing a recombinant mini-antibody specific to the human EGF-receptor with and without addition of folding promoting agents and coexpression of the molecular chaperon Skp, respectively. These conditions seemed interesting because recent works had reported, that sorbitol and betaine generate a periplasmic microenvironment supporting the folding of proteins at higher concentrations.[5,10]. In contrast to this strategy Bothmann and Pluckthun, 1998, had shown for different scFv fragments, that a coexpression of the periplasmic chaperone Skp distinctly improves their functional amounts[47]. Both strategies performed within the current invention led to a distinct increase of the functional yield of the anti-EGFR mini-antibody. The reciprocal distinct decrease in the amount of misfolded protein was simultaneously indicated by the luciferase signal.

Moreover we observed a direct correlation between the increase of the luciferase signal 2 h after induction of the mini-antibody and the product kinetic depending on the used feeding strategy and the coexpression of Skp, respectively. Interestingly, there is a lower increase in the luciferase signal if Skp is coexpressed. This may explained by the function of Skp as a periplasmic chaperone, because the coexpression of Skp is regulated by its own regulatory sequences characterized by a putitative binding site for the factor CpxR[47]. CpxR is known as a transcriptional activator of the Cpx two-component signal transduction system participating in the periplasmic stress response[27-29]. Strong increase of the luciferase signal if Skp is not expressed has been observed. On the other hand, a feeding of folding promoting agents within the short time period of 30 min. directly after the increase of the luciferase signal stopped a further increase of the luciferase signal, followed by a constant level during the rest of the fermentation process. This implies that the feeding of folding promoting agents to lead to a rapid improvement of the protein folding, whereas Skp improves the folding independent on the amount of misfolded protein.

BRIEF DESCRIPTION OF THE DRAWINGS

FIG. 1: Sequence of the degP promoter according to Wurgler and Richardson[32]. To obtain the NcoI site for the cloning of luc+ the A near the start codon has been replaced by a C (indicated with an asterisk). The lower part shows the primer for the PCR amplification of degP.

FIG. 4: The influence of different feeding strategies on protein folding, using a feeding solution resulting in a medium concentration of 6% sorbitol and 2.5 mM betaine.

FIG. 8 Promoter variants of expression plasmide pTAK-FEC ($P_{lac_C}$), pTAKFECU ($P_{lac_{CU}}$) and pTAKFECTU ($P_{lac_{CTU}}$) compared to the native lac-Promotor ($P_{lac_{nativ}}$) sequence.

CITED REFERENCES

Figure 2:
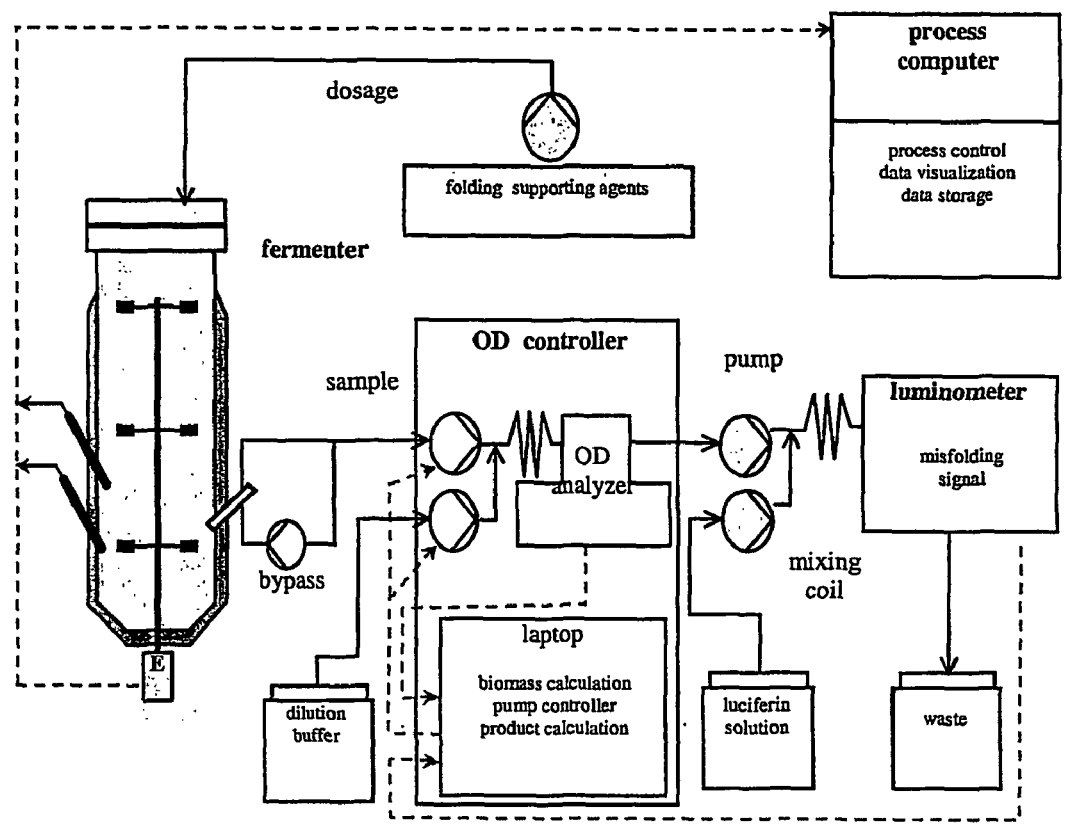
FIG. 2: Detection modul for an on-line monitoring of luciferase activity.

1. Horn U. et al. High volumetric yields of functional dimeric miniantibodies in *Escherichia coli* using an optimized expression vector and high cell density fermentation under non-limiting growth conditions. Appl. Microbiol. Biotechnol. 46, 524-532 (1996)
2. Makrides S. C. Strategies for achieving high-level expression of genes in *Escherichia coli*. Microbiol. Rev. 60, 512-538 (1996)
3. Pluckthun A. et al. Producing antibodies in *Escherichia coli*: From PCR to fermentation, in "Antibody Engineering, A practical approach", IRL press, 203-252 (1996)
4. Blackwell J. R. & Horgan R. A novel strategy for production of a highly expressed recombinant protein in an active form. FEBS Lett. 295, 10-12 (1991)
5. Lippert K. & Galinski E. A. Enzyme stabilization by ectoine-type compatible solutes: protection against heating, freezing and drying. Appl. Microbiol. Biotechnol. 37, 61-65 (1992)

6. Kets E. P., Galinski E. A., de Wit M., de Bont J. A. & Heipieper H. J. Mannitol, a novel bacterial compatible solute in *Pseudomonas putida* S12. J. Bacteriol. 178, 6665-6670 (1996)
7. Louis P. & Galinski E. A. Characterization of genes for the biosynthesis of the compatible solute ectoine from *Marinococcus halophilus* and osmoregulated expression in *Escherichia coli*. Microbiology 143, 1141-1149 (1997)
8. Wimmer H. et al. Towards a molecular level understanding of protein stabilization: the interaction between lysozyme and sorbitol. J. Biotechnol. 55, 85-100 (1997)
9. Xie G. & Timasheff S, N. Mechanism of the stabilization of ribonuclease A by sorbitol: preferential hydration is greater for the denatured then for the native protein. Protein Sci. 6, 211-221 (1997)
10. Barth S. et al. Compatible-solute-supported periplasmicexpression of functional recombinant proteins under stress conditions. Appl. Environ. Microbiol. 66, 1572-1579 (2000)
11. Missiakas D. & Raina S. Protein folding in the bacterial periplasm. J. Bacteriol. 179, 2465-71 (1997)
12. Missiakas D., Betton J. M. & Raina S, New components of protein folding in extracytoplasmic compartments of *Escherichia coli* SurA, FkpA and Skp/OmpH. Mol. Microbiol. 21, 871-884 (1996)
13. Horowitz P. M. Ironing out the protein folding problem? Nat. Biotechnol. 17, 136-137, (1999)
14. Georgiou G. & Valax P. Expression of correctly folded proteins in *Escherichia coli*. Curr. Opin. Biotechnol. 7, 190-197 (1996)
15. Nieba-Axmann S. E. & Pluckthun A. Chaperone-mediated protein folding. BIOforum international 1, 20-25 (1997)
16. Jung S. & Pluckthun A. Improving in vivo folding and stability of a single-chain Fv antibody fragment by loop grafting. Prot. Eng. 10, 959-966 (1997)
17. Pluckthun A. Studying Protein Structure and Function by Directed Evolution: Examples with Engineered Antibodies, Protein dynamics, function and design. (O. Jardetzky and J. F. LeFevre, eds), NATO ASI series, Series A (Life Sciences Vol. 301), Plenum Press, New York (1998)
18. Proba K., Worn A. Honegger A. & Pluckthun A. Antibody fragments without disulfide bonds, made by molecular evolution. J. Mol. Biol. 275, 245-253 (1998)
19. Worm A. & Pluckthun A. Mutual stabilization of VL and VH in single-chain antibody fragments, investigated with mutants engineered for stability. Biochemistry 37, 13120-13127 (1998)
20. Waldo G. S., Standish B. M., Berendzen J. & Terwilliger T. C. Rapid protein-folding assay using green fluorescent protein. Nat. Biotechnol. 17, 691-695 (1999)
21. Wigley W. C., Stidham R. D., Smith N. M., Hunt J. F. & Thomas P. J. Protein solubility and folding monitored in vivo by structural complementation of a genetic marker protein. Nat. Biotechnol. 19, 131-136 (2001)
22. Connelly L., De Las Penas A., Alba B. M. & Gross C. A. The response to extracytoplasmic stress in *Escherichia coli* is controlled by partially overlapping pathways. Genes Dev. 11, 2012-2021 (1997)
23. Danese P. N. & Silhavy T. J. The sigma(E) and the Cpx signal transduction systems control the synthesis of periplasmic protein-folding enzymes in *Escherichia coli*. Genes Dev. 11, 1183-1193 (1997)
24. Raivio T. L. & Silhavy T. J. The sigmaE and Cpx regulatory pathways: overlapping but distinct envelope stress responses. Curr. Opin. Microbiol. 2, 159-165 (1999)
25. Missiakas D., Mayer M. P., Lemaire M., Georgopoulos C. & Raina S. Modulation of the *Escherichia coli* sigmaE (RpoE) heat-shock transcription-factor activity by the RseA, RseB and RseC proteins. Mol. Microbiol. 24, 355-371 (1997)
26. De Las Penas A., Connolly L. & Gross C A. The sigmaE-mediated response to extracytoplasmic stress in *Escherichia coli* is transduced by RseA and RseB, two negative regulators of sigmaE. Mol. Microbiol. 24, 373-385 (1997)
27. Pogliano J., Lynch A. S., Belin D., Lin E. C. & Beckwith J. Regulation of *Escherichia coli* cell envelope proteins involved in protein folding and degradation by the Cpx two-component system. Genes Dev. 11, 1169-1182 (1997)
28. Raivio T. L. & Silhavy T. J. Transduction of envelope stress in *Escherichia coli* by the Cpx two-component system. J. Bacteriol. 179, 7724-7733 (1997)
29. Raivio T. L., Popkin D. L. & Silhavy T. J. The Cpx envelope stress response is controlled by amplification and feedback inhibition. J. Bacteriol. 181, 5263-5272 (1999)
30. Dartigalongue C. & Raina S. A new heat-shock gene, ppiD, encodes a peptidyl-prolyl isomerase required for folding of outer membrane proteins in *Escherichia coli*. EMBO J. 17, 3968-3980 (1998)
31. Erickson J. W. & Gross C. A. Identification of the sigma E subunit of *Escherichia coli* RNA polymerase: a second alternate sigma factor involved in high-temperature gene expression. Genes Dev. 3, 1462-1471 (1989)
32. Wurgler S. M. & Richardson C. C. Structure and regulation of the gene for dGTP triphosphohydrolase from *Escherichia coli*. Proc. Natl. Acad. Sci. U.S.A. 87, 2740-2744 (1990)
33. Rouviere P. E. et al. rpoE, the gene encoding the second heat-shock sigma factor, sigma E, in *Escherichia coli*. EMBO J. 14, 1032-1042 (1995)
34. Raina S., Missiakas D. & Georgopoulos C. The rpoE gene encoding the sigma E (sigma 24) heat shock sigma factor of *Escherichia coli*. EMBO J. 14, 1043-1055 (1995)
35. De Las Penas A., Connolly L. & Gross C. A. sigmaE is an essential sigma factor in *Escherichia coli*. J. Bacteriol. 179, 6862-6864 (1997)
36. Lipinska B., Sharma S. & Georgopoulos C. Sequence analysis and regulation of the htrA gene of *Escherichia coli*: a sigma 32-independent mechanism of heat-inducible transcription. Nucleic Acids Res. 16, 10053-10067 (1988)
37. Lipinska B., Fayet O., Baird L. & Georgopoulos C. Identification, characterization, and mapping of the *Escherichia coli* htrA gene, whose product is essential for bacterial growth only at elevated temperatures. J. Bacteriol. 171, 1574-1584 (1989)
38. Strauch K. L., Johnson K. & Beckwith J. Characterization of degP, a gene required for proteolysis in the cell envelope and essential for growth of *Escherichia coli* at high temperature. J. Bacteriol. 171 2689-2696 (1989)
39. Lipinska B., Zylicz M. & Georgopoulos C. The HtrA (DegP) protein, essential for *Escherichia coli* survival at high temperatures, is an endopeptidase. J. Bacteriol. 172, 1791-1797 (1990)
40. Danese P. N., Snyder W. B., Cosma C. L., Davis L. J. & Silhavy T. J. The Cpx two-component signal transduction pathway of *Escherichia coli* regulates transcription of the gene specifying the stress-inducible periplasmic protease, DegP. Genes Dev. 9, 387-398 (1995)
41. Larsen J. E. L., Gerdes K., Light J. & Molin S. Low-copy-number plasmid-cloning vectors amplifiable by derepression of an inserted forgein promoter. Gene 28, 45-54 (1984)

42. Krebber A., Burmester J. & Pluckthun A. Inclusion of an upstream transcriptional terminator in phage display vectors abolishes background expression of toxic fusions with coat protein g3p. Gene 178, 71-74 (1996)
43. Nordstrom K., Molin S. & Aagaard-Hansen H. Partitioning of plasmid R1 in *Escherichia coli*. I. Kinetics of loss of plasmid derivatives deleted of the par region. Plasmid 4, 215-227 (1980)
44. Nordstrom K., Molin S. & Aagaard-Hansen H. Partitioning of plasmid R1 in *Escherichia coli*. II. Incompatibility properties of the partitioning system. Plasmid 4, 332-339 (1980)
45. Danese P. N. & Silhavy T. J. CpxP, a stress-combative member of the Cpx regulon. J Bacteriol 180, 831-839 (1998).
46. Ades S. E., Connolly L. E., Alba B. M. & Gross C. A. The *Escherichia coli* sigma(E)-dependent extracytoplasmic stress response is controlled by the regulated proteolysis of an anti-sigma factor. Genes Dev. 13, 2449-2461 (1999)
47. Bothmann H. & Pluckthun A. Selection for a periplasmic factor improving phage display and functional periplasmic expression. Nat. Biotechnol. 16, 376-380 (1998)
48. S. Barth, M. Huhn, B. Matthey, A. Klimka, E. A. Galinski and A. Engert: "Compatible-Solute-Supported Periplasmic Expression of Functional Recombinant Proteins under Stress Conditions" Appl. Env. Microbiol., 66, 1572-1579, (2000)
49. Wimmer H, Olsson M, Petersen M T, Hatti-Kaul R, Peterson S B, Muller N.; Towards a molecular level understanding of protein stabilization: the interaction between lysozyme and sorbitol. J. Biotechnol. 55:85-100, (1997)
50. Xie G, Timasheff S N. Mechanism of the stabilization of ribonuclease A by sorbitol: preferential hydration is greater for the denatured then for the native protein. Protein Sci. 1, 211-21, (1997)

The following Examples describe the invention in more detail without limiting it.

Example 1

Vector constructions. The mini-antibody expression vector pTAKFECU is derived from the previously described expression vectors p41FEG1T[3] and pAK100[3]. The vector pTAKFECU contains the chloramphenicol resistance gene (cat) of pAK100 and the strong lacUV5 promoter, introduced by site directed mutagenesis by means of the Muta-Gene™ phagemid kit (BioRad Laboratories, Richmond, U.S.A.). The Skp coexpressing plasmid pHBFECU was derived by inserting the MluI-HindIII fragment of pTAKFECU encoding the lacUV5 promoter and the antiEGFR mini-antibody into pHB110[47]. The luciferase gene of pSG-luc+ (Promega GmbH, Germany) was inserted into pTrc99A (Amersham Pharmacia Biotech, Germany) via the restriction sites NcoI and XbaI resulting in pTrc-luc+ To construct the degP-luciferase reporter plasmid plt1, a synthetic polylinker with the cloning sites for the tHP-terminator (KpnI, NsiI)[42], the degP-promotor (NsiI, NcoI) and the luciferase reporter gen luc+ (NcoI, XbaI) was inserted into the EcoRI and HindIII sites of pUC18, resulting in pUC18PL. The tHP-terminator was obtained from pTAKFECU. The degP-promotor was cloned following PCR amplification from genomic DNA of *Escherichia coli* MG1655 (ATCCno. 47076) (primers are depicted in FIG. 1). The PCR product includes the complete DNA sequence from the stop codon of the dGTPase gene (dgt) located upstream from degP to the start codon of degP (FIG. 1). The luciferase gen luc+ was obtained from pSG-luc+ The resulting luciferase reporter cassette was cloned into pOU61[41] via the unique restriction sites EcoRI and BamHI, resulting the degP-luciferase reporter vector plt1.

Example 2

Design of the degp-luciferase reporter vector plt1 is based on the plasmid pOU61[41]. Its genetically modified R1 origin is compatible with the colE1 derivate used in the cotransformed second plasmid for the expression of recombinant protein. The luciferase cassette contains the degP-promoter (complete DNA sequence from the stop codon of the dGTPase gene (dgt) located upstream from degp to the start codon of degP) and downstream followed by the reporter gene luciferase luc+ (FIG. 1). In addition to this we inserted a tHP terminator (decreasing transcriptional read-through of upstream located genes up to five fold.[42]) upstream of degP. The resulting degP-luciferase cassette was cloned into pOU61, thus obtaining the vector plt1.

Example 3

Determination of luciferase activity in cell suspensions of *Escherichia coli*. We constructed the plasmid pTrc-luc+, allowing an induction of luciferase with IPTG, to develop a functional assay for the determination of luciferase activity in *Escherichia coli*. Several approaches to determine the luciferase activity were made, including cell disruption by sonication and treatment with different toluene concentrations to make the cell wall more permeable to luciferine. Fortunately, untreated cells show comparable luciferase activity to disrupted cells. This indicates, that luciferine can diffuse through the *Escherichia coli* cell wall. In this respect we determined the luciferase activity in subsequent assays by adding buffered luciferine solution directly to the cell suspension. The measured luciferase signal was referred to as relative luciferase units (RLU).

Example 4

Detection device for on-line monitoring of luciferase activity. The sampling system is based on a fermenter bypass coupled to a peristaltic pump. The sampling was started with a continuous predilution of the fermenter probe using 0.9% NaCl. Several experiments indicated an optimal predilution rate of 1:50, depending on the cell density at the starting point of the measurements (in our case $OD_{550}=90$). A further dilution providing a constant and exact $OD_{550}=0.4$ is necessary for the on-line monitoring of the luciferase activity. This was achieved by developing of an OD-controller consisting of a flow through photometer to determine the actually OD of the predilution and a laptop to calculate the speed of a sample pump and a dilution pump. The diluted sample was mixed with a buffered luciferine solution by using a further pump with a constant speed and injected in a flow through luminometer to determine the luciferase activity. The total time of one analysis was 90 s (FIG. 2).

Example 5

Figure 3:
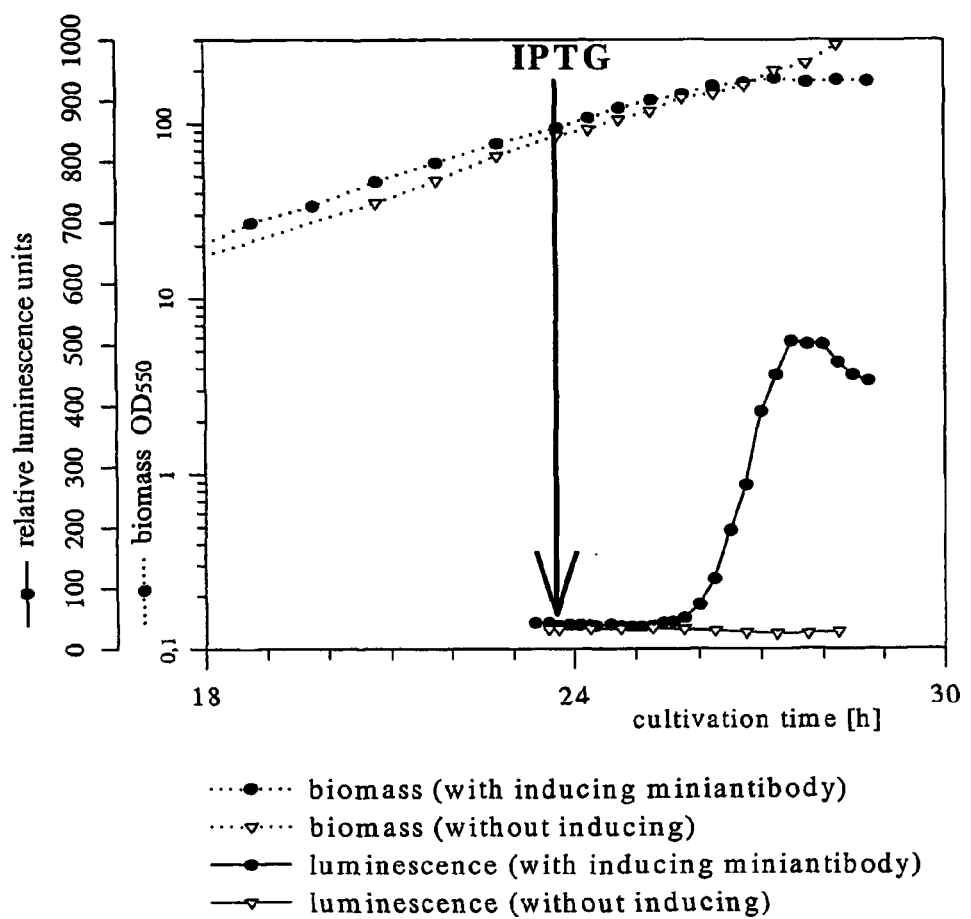
FIG. 3: The basal and maximum level of the reporter system, determining the luciferase activity under non-inducing and inducing conditions, respectively.
Figure 5:
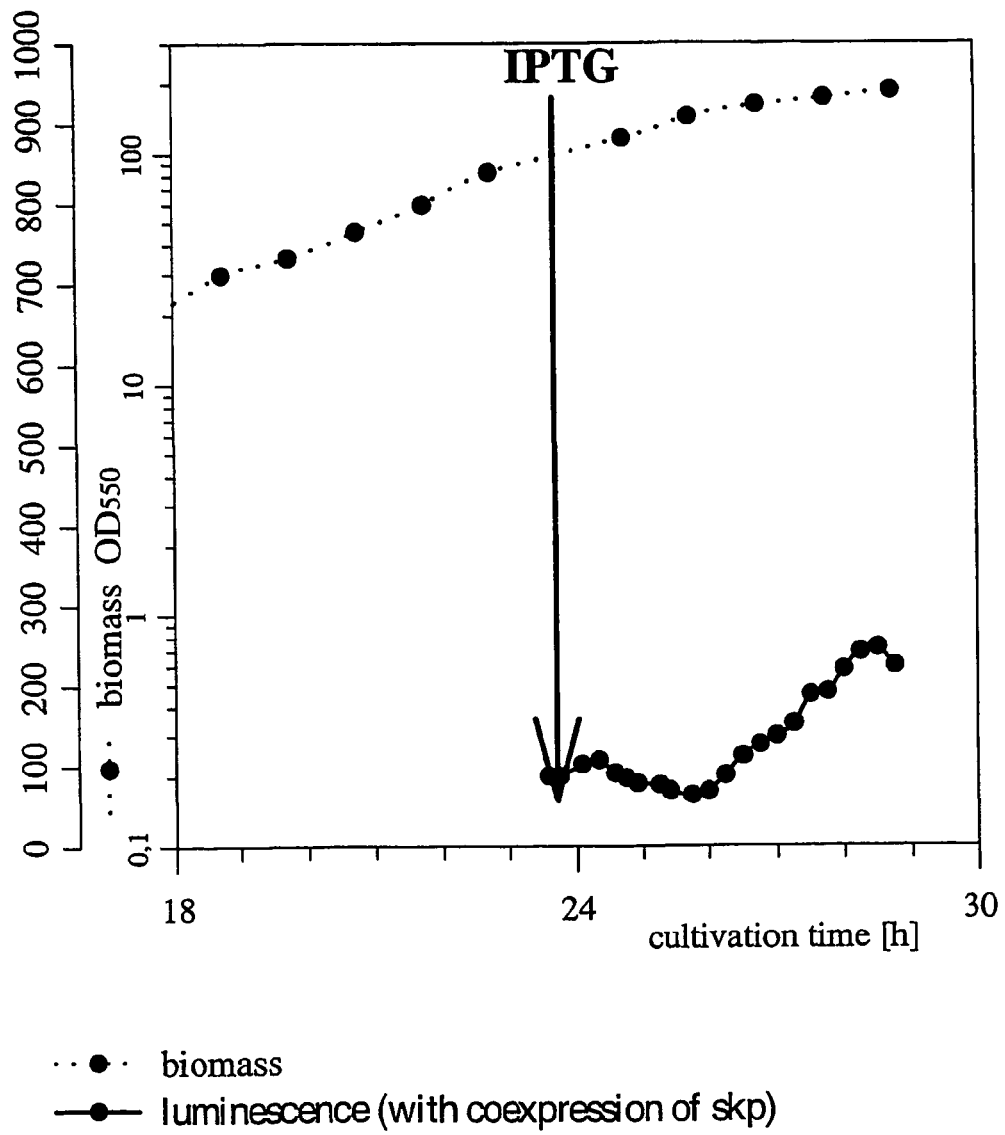
FIG. 5: The influence of a coexpression of the periplasmic chaperone Skp on protein folding.

High cell density cultivation (HCDC) was performed in a 10 L stirred bioreactor according to Horn et al.[1] using a glucose mineral salt medium. All fermentations were carried out under the same conditions including a temperature of 26.degree. C., a starting $OD_{550}=0.2$ and the adding of IPTG at $OD_{550}=90$. Furthermore, the precultures were inoculated with glycerol preserves of the same stock. The feeding of glucose was performed using a glucose flow injection analysis allowing a non-limited growth of the cells during the whole fermentation in order to avoid any additional stress. After a cultivation time of 29 h including an induction period of 5 h we achieved final cell densities in a range of $OD_{550}=110$ corresponding to dry biomasses of 25 gL$^{-1}$ (FIG. 3-5).

Example 6

On-line monitoring of misfolded protein was analysed by expression f a recombinant miniantibody specific to the human EGF-receptor. The miniantibody consists of the scfv fragment with a C-terminally fused hinge followed by a helix-turn-helix motif, which homodimerizes in vivo. The miniantibody is encoded by the plasmid pTAKFECU derived from our previously described expression vectors p41FEG1T and pAK100[3]. The expression was performed in Escherichia coli RV308 (ATCC no. 31608). This strain is especially suitable for HCDC because of its drastically decreased rate of acetat formation. Escherichia coli RV308 was cotransformed with pTAKFECU and the degP-luciferase reporter vector phi as a dual plasmid system to evaluate the ratio of misfolded miniantibodies.

Figure 6:
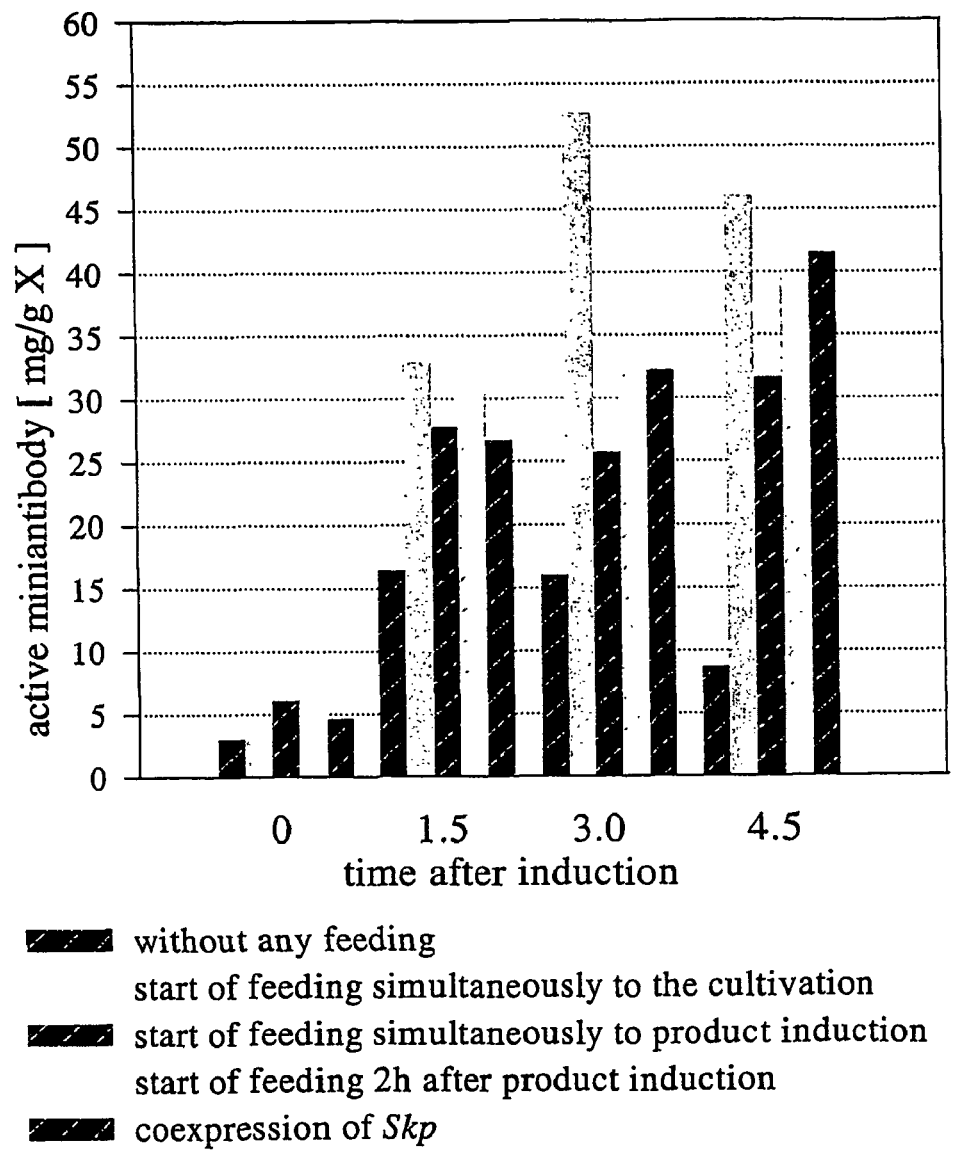
FIG. 6: Kinetic of the formation of functional miniantibodies depending on the used feeding strategy and the coexpression of Skp.

The basal and maximum level of luciferase activity was determined to evaluate the working range of our system. For this purpose a first fermentation under non-inducing conditions was compared with an IPTG induced expression of the miniantibody. The luciferase activities were determined every 15 minutes. The measurements were started at a cell density of $OD_{550}=75$ for both fermentations, but the induction of the miniantibody in the second fermentation started 30 minutes later at an $OD_{550}=90$. For the non-induced culture only a low basal level of about 40 relative luminescence units (RLU) during the whole fermentation was determined. In the first phase after induction of the miniantibody the luciferase signal was comparable to non-induced culture. In contrast to this we obtained a strong increase of the luciferase signal 2 h after induction corresponding to the product formation kinetic of functional miniantibody (FIG. 3, FIG. 6).

We tested three different feeding strategies, using a feeding solution resulting in a medium concentration of 6% sorbitol and 2.5 mM betaine to determine the influence of folding promoting agents on the ratio of misfolded miniantibody. The luciferase signal reached only the basal level in case of feeding either at the beginning of the fermentation or simultaneously to the induction. However, when the feeding solution was added 2 h after the induction corresponding to the start of the product formation there was an increase in the luciferase signal comparable to the induced cultivation without any feeding, followed by a constant level of about 170 RLU during the rest of the cultivation (FIG. 4).

In addition to this we analysed the influence of a coexpression of the periplasmic chaperone Skp on a mini-antibody expression. For this purpose the DNA sequence of the miniantibody including the lacUV5 promoter region and the pelB signal sequence was cloned into pHB110 encoding Skp. The resulting plasmid pHBFECU was cotransformed with plt1 into Escherichia coli RV308. Similar to both the cultivation without and with feeding of folding promoting agents at the starting point of product formation we obtained the increase in the luciferase signal 2 h after the induction. In contrast to these cultivations in the Skp coexpression the obtained increase of the gradient was lower and reached a maximum of 230 RLU comparable only to the one with feeding of folding promoting solution at the starting point of product formation (FIG. 5).

Example 7

On-line monitoring of luciferase activity. The sampling system used for the on-line monitoring of the luciferase activity is illustrated in FIG. 2. The fermenter bypass was performed by a peristaltic pump (504U, Watson Marlow, Falmouth, England) followed by a continuous predilution of the fermentor sample with 0.9% NaCl at a ratio of 1:50 using a four channel peristaltic pump MS-CA4/840 (Ismatec GmbH, Wertheim-Mondfeld, Germany). The OD-controller is based on a flow through photometer (VIS Jenway 6300, Jenway Inc., Princeton, U.S.A.) to determine the actually OD of the predilution and a laptop to calculate the speed of a sample and dilution pump (peristaltic pumps ISM Reglo 12/100, Ismatec GmbH, Wertheim-Mondfeld, Germany). The values were calculated using the software Dasylab (GBMmbH, Monchengladbach, Germany). A fermenter sample with a constant $OD_{550}$ nm=0.4 was mixed with a luciferin solution at a ratio of 1:1. For this purpose 5 mg D-luciferin sodium salt was dissolved in 1250 μl $H_2O$. 100 μl of this solution was added to 9.9 ml of luciferin buffer, containing 25 mM Tricine, 15 mM $MgCl_2$, 5 mM ATP, 7 mM Mercaptoethanol and 5 mg BSA at pH 7.8. 0.5 ml of the luciferin solution are needed for one analysis. The luciferase activity was measured with a flow through luminescence detector LEO (Wallac GmbH, Freiburg, Germany) and calculated using the software Dasylab (GBMmbH, Monchengladbach, Germany). The measured luciferase signal was referred to as relative luciferase units (RLU).

Example 8

Figure 7:
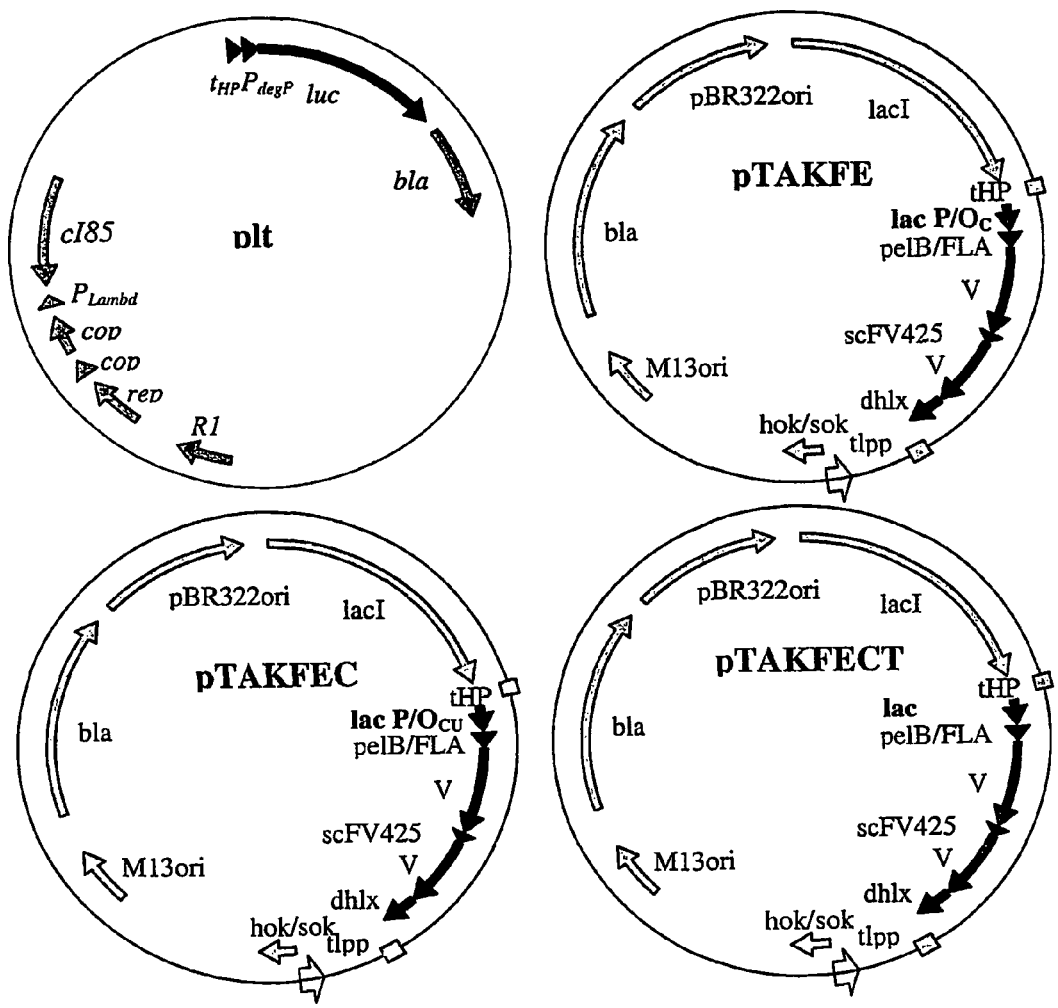
FIG. 7 DegP-luciferase reporterplasmid plt1 and expression plasmide pTAKFEC, pTAKFECU and pTAKFECTU. The expression plasmids differ in modified lac P/O-sequences.
Figure 9:
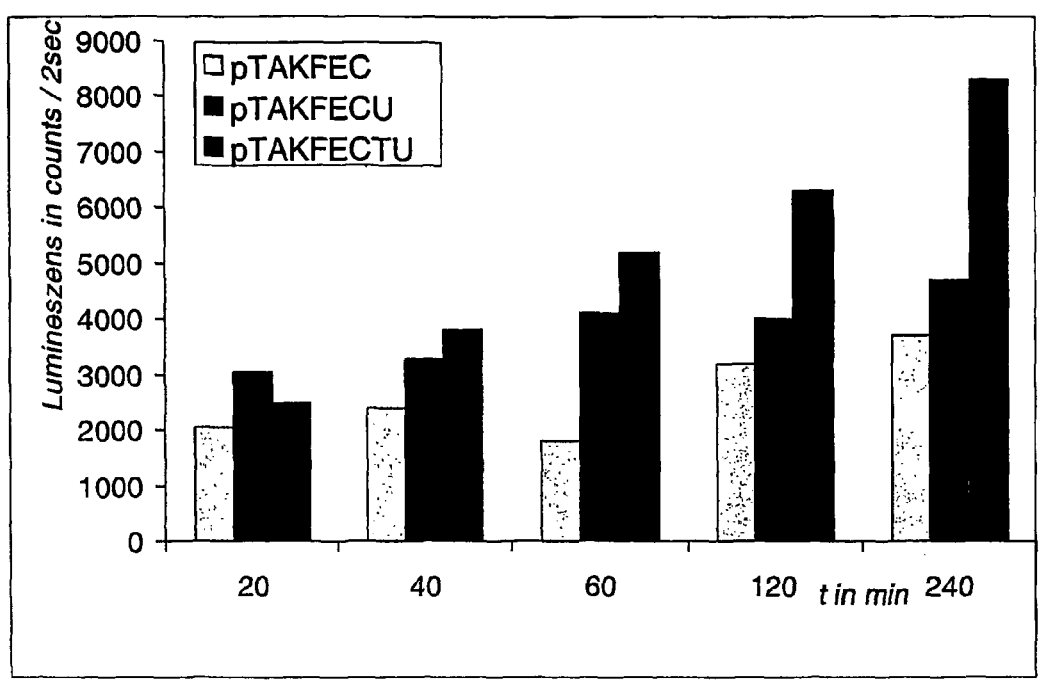
FIG. 9 Lumineszenz correlated with the promoter strength of the used expression plasmides.

Miniaturized assay for optimization of paralleled protein expression and monitoring of protein folding. The basic principle described for monitoring and optimizing protein has been adapted to microvolumes to bring it to the format of a microtitre plate or even smaller. The test system comprised the antiEGFR-mini-antibody. As described above the reporter plasmid plt1 with plasmides pTAKFEC, pTAKFECU and pTAKFECTU have been used to co-transform Escherichia coli K12 RV308. The plasmide comprise variants of the lac-promotors, thus allowing the differential expression of mini-antibody as shown in FIGS. 7 and 8. Measuring the luciferase activity of the reporter protein plt1 indicated that the portion of misfolded protein correlated with individual promoter used as shown in FIG. 9. Thus the plasmid encoded plt1 reporter system is useful for optimizing the expression with respect to the individual promoter to be selected.

Cultivation in microtiter plates was performed in 100 μl mineral salt medium (Horn et al., 1996 at a temperature of 26° C. using a heatable microtiter plate shaker—Thermostar (Fa. DMG Medizintechnik GmbH, Offenburg, Germany). The inocculation of the master plates was performed using 10 μl of a Glycerol stock solution of the individual strains. Result are show in (FIG. 3) and have been performed as triplicates. Estimation of Luciferase activity has been measured after adding 100 μl Luciferin-Losung and was measured with a Chemoluminaszenzreader Victor 1420 Multilabel Counter (Fa. Wallac GmbH, Freiburg, Germany). For measuring the kinetik given in FIG. 9 the luciferase activity has been evaluated in paralleled cultures at time points given.

Example 9

Correlation of luciferase signal to the ratio of functional mini-antibodies. The amount of functional mini-antibodies was determined using an ELISA, based on the extracellular domain of the human EGF receptor. Samples of the cells expressing the mini-antibody at 0h, 1.5 h, 3.0 h and 4.5 h were analyzed in order to obtain a product kinetic. The results show a distinctly improved yield of functional mini-antibodies, depending on the used feeding strategy of folding promoting agents (FIG. 6). This indicates that the determined luciferase signal for misfolded mini-antibody is indirectly proportional to the amount of functional mini-antibodies.

Example 10

Quantitative determination of the functional amount of the mini-antibodies. The amounts of functional antiEGFR mini-antibodies were determinated by a functional enzyme-linked immunosorbant assay (ELISA) according to Horn et al[1] using the extra-cytoplasmic domain of the human EGFR (Merck KgaA, Darmstadt, Gemany).

The invention claimed is:

1. A method for the rapid monitoring of functionally correct folding or misfolding of a target protein produced by a recombinant process in a bacterial host by means of the reporter enzyme luciferase, comprising:

(i) expressing a target protein in said recombinant bacterial host cell expression system using a first plasmid comprising a gene coding for the target protein, (ii) expressing luciferase in said recombinant bacterial host cell expression system using a second plasmid in said host cell comprising the reporter gene luc+ which codes for luciferase and is under control of the DegP promoter, and (iii) detecting and analysing on-line during the fermentation process of said bacterial host cell without disrupting the host cell, the expressed luciferase signals, which are correlated to the correct folding or misfolding of the co-expressed target protein thereby determining the presence of correct folding or misfolding thereof within a total time of 90 seconds per analysis.

2. The method of claim 1, wherein the second plasmid contains a gene construct comprising the complete DNA sequence of the DegP promoter followed in downstream direction by the DNA sequence of the luc+ gene.

3. The method of claim 2, wherein said gene construct contains a terminator sequence, that is located upstream of the DegP promoter sequence.

4. The method according to claim 1, wherein the production of the DegP promoter luc+ gene product is monitored by a kinetic measurement process.

5. The method of claim 1, wherein said bacterial host cell is *E. coli*.

6. The method of claim 1, wherein during co-expression of the target protein and said reporter enzyme an agent is applied that promotes correct protein folding.

7. The method of claim 1, wherein said target protein is a miniantibody.

8. The method of claim 7, wherein said miniantibody is an anti-EGFR miniantibody.

9. A method for producing a functional, correctly folded target protein produced in a recombinant bacterial host cell expression system comprising:
(i) monitoring folding of the target protein according to the method of claim 1,
(ii) modulating protein folding by co-expressing or adding to the host cell one or more agents that promote functionally correct target protein folding, and
optionally
(iii) repeating step (i) and (ii) until an optimum of functional-correctly folded target protein is obtained.

10. The method of claim 9 wherein said agent is the periplasmatic chaperone Skp.

11. The method of claim 9, wherein said agent is a polyole and/or a betaine derivative.

12. The method of claim 9, wherein said agent is selected from the group consisting of glycerol, sorbitol, glycine betaine and hydroxyectoine.

13. The method of claim 9, wherein said bacterial host cell is *E. coli*.

14. The method of claim 9, wherein the target protein is a miniantibody.

15. The method of claim 14, wherein said miniantibody is an anti-EGFR miniantibody.

* * * * *

SEQUENCE LISTING

```
<160> NUMBER OF SEQ ID NOS: 8

<210> SEQ ID NO 1
<211> LENGTH: 135
<212> TYPE: PRT
<213> ORGANISM: Artificial
<220> FEATURE:
<223> OTHER INFORMATION: Sequence of the degP promotor according to
      Wurgler and Richardson32. degP - Promotor . dgt SD start degP

<400> SEQUENCE: 1

Thr Ala Ala Cys Cys Ala Gly Gly Cys Thr Thr Thr Thr Gly Thr Ala
1               5                   10                  15

Ala Ala Gly Ala Cys Gly Ala Ala Cys Ala Ala Thr Ala Ala Ala Thr
            20                  25                  30

Thr Thr Thr Thr Ala Cys Cys Thr Thr Thr Thr Gly Cys Ala Gly Ala
        35                  40                  45

Ala Ala Cys Thr Thr Thr Ala Gly Thr Thr Cys Gly Gly Ala Ala Cys
    50                  55                  60

Thr Thr Cys Ala Gly Gly Cys Thr Ala Thr Ala Ala Ala Cys Gly
65                  70                  75                  80

Ala Ala Thr Cys Thr Gly Ala Ala Gly Ala Ala Cys Ala Cys Ala Gly
            85                  90                  95

Cys Ala Ala Thr Thr Thr Thr Gly Cys Gly Thr Thr Ala Thr Cys Thr
            100                 105                 110

Gly Thr Thr Ala Ala Thr Cys Gly Ala Gly Ala Cys Thr Gly Ala Ala
        115                 120                 125

Ala Thr Ala Cys Ala Thr Gly
    130                 135

<210> SEQ ID NO 2
<211> LENGTH: 140
<212> TYPE: PRT
<213> ORGANISM: Artificial
<220> FEATURE:
<223> OTHER INFORMATION: Sequence of the degP promotor according to
      Wurgler and Richardson32. * start luc+

<400> SEQUENCE: 2

Thr Ala Ala Cys Cys Ala Gly Gly Cys Thr Thr Thr Thr Gly Thr Ala
1               5                   10                  15

Ala Ala Gly Ala Cys Gly Ala Ala Cys Ala Ala Thr Ala Ala Ala Thr
            20                  25                  30

Thr Thr Thr Thr Ala Cys Cys Thr Thr Thr Thr Gly Cys Ala Gly Ala
        35                  40                  45

Ala Ala Cys Thr Thr Thr Ala Gly Thr Thr Cys Gly Gly Ala Ala Cys
    50                  55                  60

Thr Thr Cys Ala Gly Gly Cys Thr Ala Thr Ala Ala Ala Ala Cys Gly
65                  70                  75                  80
```

```
Ala Ala Thr Cys Thr Gly Ala Ala Gly Ala Cys Ala Cys Ala Gly
            85                  90                  95

Cys Ala Ala Thr Thr Thr Thr Gly Cys Gly Thr Thr Ala Thr Cys Thr
            100                 105                 110

Gly Thr Thr Ala Ala Thr Cys Gly Ala Ala Thr Cys Gly Ala Cys Cys
        115                 120                 125

Ala Thr Gly Gly Ala Ala Gly Ala Cys Gly Cys Cys
    130                 135                 140
```

<210> SEQ ID NO 3
<211> LENGTH: 31
<212> TYPE: PRT
<213> ORGANISM: Artificial
<220> FEATURE:
<223> OTHER INFORMATION: Sequence of the degP promotor according to
      Wurgler and Richardson[32]. degP_fw:

<400> SEQUENCE: 3

```
Thr Gly Cys Ala Thr Gly Cys Ala Thr Cys Cys Ala Gly Gly Cys Thr
1               5                   10                  15

Thr Thr Thr Gly Thr Ala Ala Ala Gly Ala Cys Gly Ala Ala Cys
            20                  25                  30
```

<210> SEQ ID NO 4
<211> LENGTH: 37
<212> TYPE: PRT
<213> ORGANISM: Artificial
<220> FEATURE:
<223> OTHER INFORMATION: Sequence of the degP promotor according to
      Wurgler and Richardson[32]. degP_back:

<400> SEQUENCE: 4

```
Thr Cys Ala Thr Gly Cys Cys Ala Thr Gly Gly Ala Thr Thr Thr Cys
1               5                   10                  15

Ala Gly Thr Cys Thr Cys Gly Ala Thr Thr Ala Ala Cys Ala Gly Ala
            20                  25                  30

Thr Ala Ala Cys Gly
        35
```

<210> SEQ ID NO 5
<211> LENGTH: 80
<212> TYPE: PRT
<213> ORGANISM: Artificial
<220> FEATURE:
<223> OTHER INFORMATION: Promotor Plac_native

<400> SEQUENCE: 5

```
Cys Cys Cys Ala Cys Cys Thr Cys Ala Ala Cys Gly Cys Ala Ala Thr
1               5                   10                  15

Thr Ala Ala Thr Gly Thr Gly Ala Gly Thr Thr Ala Gly Cys Thr Cys
            20                  25                  30

Ala Cys Thr Cys Ala Thr Thr Ala Gly Gly Cys Ala Cys Cys Cys Cys
        35                  40                  45

Ala Gly Gly Cys Thr Thr Thr Ala Cys Ala Cys Thr Thr Thr Ala Thr
    50                  55                  60

Gly Cys Thr Thr Cys Cys Gly Gly Cys Thr Cys Gly Thr Ala Thr Gly
65                  70                  75                  80
```

<210> SEQ ID NO 6
<211> LENGTH: 80
<212> TYPE: PRT
<213> ORGANISM: Artificial
<220> FEATURE:

-continued

```
<223> OTHER INFORMATION: Promotor Plac_C

<400> SEQUENCE: 6

Cys Cys Cys Ala Cys Cys Thr Cys Ala Ala Cys Gly Cys Ala Ala Thr
1               5                   10                  15

Thr Ala Ala Thr Gly Thr Ala Ala Gly Thr Thr Ala Gly Cys Thr Cys
                20                  25                  30

Ala Cys Thr Cys Ala Thr Thr Ala Gly Gly Cys Ala Cys Cys Cys Cys
            35                  40                  45

Ala Gly Gly Cys Thr Thr Thr Ala Cys Ala Cys Thr Thr Thr Ala Thr
        50                  55                  60

Gly Cys Thr Thr Cys Cys Gly Gly Cys Thr Cys Gly Thr Ala Thr Gly
65                  70                  75                  80

<210> SEQ ID NO 7
<211> LENGTH: 80
<212> TYPE: PRT
<213> ORGANISM: Artificial
<220> FEATURE:
<223> OTHER INFORMATION: Promotor Plac_CU

<400> SEQUENCE: 7

Cys Cys Cys Ala Cys Cys Thr Cys Ala Ala Cys Gly Cys Ala Ala Thr
1               5                   10                  15

Thr Ala Ala Thr Gly Thr Gly Ala Gly Thr Thr Ala Gly Cys Thr Cys
                20                  25                  30

Ala Cys Thr Cys Ala Thr Thr Ala Gly Gly Cys Ala Cys Cys Cys Cys
            35                  40                  45

Ala Gly Gly Cys Thr Thr Thr Ala Cys Ala Cys Thr Thr Thr Ala Thr
        50                  55                  60

Gly Cys Thr Thr Cys Cys Gly Gly Cys Thr Cys Gly Thr Ala Thr Ala
65                  70                  75                  80

<210> SEQ ID NO 8
<211> LENGTH: 77
<212> TYPE: PRT
<213> ORGANISM: Artificial
<220> FEATURE:
<223> OTHER INFORMATION: Promotor Plac_CTU

<400> SEQUENCE: 8

Cys Cys Cys Ala Cys Cys Thr Cys Ala Ala Cys Gly Cys Ala Ala Thr
1               5                   10                  15

Thr Ala Ala Thr Gly Thr Gly Ala Gly Thr Thr Ala Gly Cys Thr Cys
                20                  25                  30

Ala Cys Thr Cys Ala Thr Thr Ala Gly Gly Cys Ala Cys Cys Cys Cys
            35                  40                  45

Ala Gly Gly Thr Thr Gly Ala Cys Ala Ala Thr Ala Thr Gly Cys Thr
        50                  55                  60

Thr Cys Cys Gly Gly Cys Thr Cys Gly Thr Ala Thr Ala
65                  70                  75
```